US006986895B2

(12) United States Patent
Suares et al.

(10) Patent No.: US 6,986,895 B2
(45) Date of Patent: Jan. 17, 2006

(54) THICKENED COSMETIC COMPOSITIONS

(75) Inventors: Alan Joseph Suares, Cheshire, CT (US); Joanna Hong Zhang, Milford, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 563 days.

(21) Appl. No.: 10/056,923

(22) Filed: Jan. 24, 2002

(65) Prior Publication Data
US 2003/0118619 A1 Jun. 26, 2003

Related U.S. Application Data

(60) Provisional application No. 60/318,687, filed on Sep. 12, 2001.

(51) Int. Cl.
*A61K 6/00* (2006.01)

(52) U.S. Cl. .................. 424/401; 514/772.4; 514/557; 514/613

(58) Field of Classification Search ............... 424/401, 424/78.08, 70.11; 514/772.4, 557, 613
See application file for complete search history.

(56) References Cited

U.S. PATENT DOCUMENTS

| 5,422,112 A | 6/1995 | Williams |
| 5,863,545 A * | 1/1999 | Griat ......................... 424/401 |
| 5,874,095 A | 2/1999 | Deckner et al. |
| 5,879,718 A | 3/1999 | Sebillote-Arnaud |
| 5,891,452 A | 4/1999 | Sebillote-Arnaud et al. |
| 5,908,618 A | 6/1999 | Lorant |
| 5,952,395 A | 9/1999 | Lorant |
| 6,120,780 A | 9/2000 | Dupuis et al. |
| 6,123,960 A | 9/2000 | Favre et al. |
| 6,149,900 A | 11/2000 | Afriat et al. |
| 6,180,118 B1 | 1/2001 | Maubru |
| 6,239,174 B1 | 5/2001 | Afriat et al. |
| 6,287,543 B1 | 9/2001 | Terren et al. |
| 6,294,186 B1 * | 9/2001 | Beerse et al. ............... 424/405 |
| 6,375,959 B1 | 4/2002 | Mallo et al. |
| 6,437,068 B2 | 8/2002 | Loffler et al. |
| 6,468,549 B1 | 10/2002 | Dupuis et al. |
| 6,682,750 B2 * | 1/2004 | Loffler et al. ............... 424/401 |
| 2001/0029287 A1 | 10/2001 | Loffler et al. |
| 2002/0058055 A1 | 5/2002 | Zecchino et al. |
| 2002/0155076 A1 | 10/2002 | Lanzendorfer et al. |

FOREIGN PATENT DOCUMENTS

| EP | 0 522 756 | 1/1996 |
| EP | 0 815 845 | 6/1997 |
| EP | 0 815 845 B1 | 1/1998 |
| EP | 1 116 733 | 7/2001 |
| EP | 1 216 686 | 12/2001 |
| EP | 1 216 695 | 12/2001 |
| WO | 00/32639 | 6/2000 |
| WO | 01/28338 | 4/2001 |
| WO | 01/62214 | 8/2001 |
| WO | 02/051377 | 7/2002 |

OTHER PUBLICATIONS

Seppic, Sepigel®—Simulgel® Formulator's essential partners brochure—2001.
Clariant—Aug. 2000, Mar. 2001 and Jan. 2001—R&D Personal Care—4 sheets.
InCosmetics, Dusseldorf, Apr. 2001, "Aristoflex AVC: A New pH Stable Polymer for Gels and O/W Emulsions" by Matthias Loffler, Dennis Miller, pp. 1-16.
Clariant, Jan. 2001, "Aristoflex AVC"—3 pages.

* cited by examiner

*Primary Examiner*—Thurman K. Page
*Assistant Examiner*—Blessing Fubara
(74) *Attorney, Agent, or Firm*—Milton L. Honig

(57) ABSTRACT

A cosmetic composition is provided which includes an alpha- or beta-hydroxycarboxylic acid at least partially neutralized and a taurate copolymer in a low pH system. The taurate copolymer improves skinfeel and provides viscosity to the system.

2 Claims, No Drawings

THICKENED COSMETIC COMPOSITIONS

This application claims benefit of Provisional Application No. 60/318,687 filed Sep. 12, 2001.

BACKGROUND OF THE INVENTION

1. Field of the Invention

The invention relates to improved thickening systems for cosmetic compositions, particularly those in lotion and cream form.

2. The Related Art

Aqueous cosmetic compositions often require thickeners to achieve an aesthetically pleasing viscosity. Fluids that flow with a watery consistency too rapidly run off the treated skin areas. For a cosmetic to be effective, it often must have substantivity. Thickeners provide this substantivity. Furthermore, low viscosity formulas which may be skin effective nevertheless through their wateriness signal ineffectiveness to the consumer. Products of watery consistency are also aesthetically displeasing to consumers with expectations of rich and creamy products.

U.S. Pat. No. 5,422,112 (Williams) discloses a triple thickener system including xanthan gum, magnesium aluminum silicate and polyacrylamide. The compositions are said to be particularly effective for thickening alpha-hydroxy carboxylic acids and salts thereof, especially at low pH.

U.S. Pat. No. 5,874,095 (Deckner et al.) reports an enhanced skin penetration system for improved topical delivery of drugs. Essential to the system is a nonionic polyacrylamide of high molecular weight described as effective at low pH.

U.S. Pat. No. 5,952,395 (Lorant) and U.S. Pat. No. 5,891,452 (Sebillote-Arnaud et al.) describe cosmetic compositions gelled into an emulsion with a cross-linked poly (2-acrylamido-2-methylpropanesulfonic acid).

Countless numbers of other thickening agents are known in the literature. Perhaps this plethora intimates that not all thickening agents are equally effective for any particular type of formulation.

Indeed, there are some formulations which are extremely difficult to thicken, and even if initially thickened may have storage stability problems. Low pH systems are particularly sensitive and difficult.

Accordingly, it is an object of the present invention to provide a thickener system and thickened cosmetic compositions of sufficiently aesthetically pleasing viscosity and skinfeel.

It is another object of the present invention to provide thickening systems for cosmetic compositions that are effective at low pH.

It is still another object of the present invention to provide thickening systems for water and oil emulsion cosmetic compositions that also function as stabilizers preventing phase separation.

These and other objects of the present invention will more readily become apparent from the description and examples which follow.

SUMMARY OF THE INVENTION

A cosmetic composition is provided which includes:
(i) from about 0.01 to 20% of a $C_1$–$C_{25}$ alpha- or beta-hydroxycarboxylic acid at least partially present as a salt thereof;
(ii) from about 0.01 to about 10% of a taurate copolymer; and
(iii) a cosmetically acceptable carrier, wherein the composition has a pH of less than about 6.

DETAILED DESCRIPTION OF THE INVENTION

Now it has been discovered that taurate copolymers are highly effective thickening agents for low pH cosmetic compositions. This system is particularly useful for building viscosity in relatively acidic compositions, especially those containing $C_1$–$C_{25}$ alpha- or beta-hydroxycarboxylic acids. Beyond building viscosity, the thickening system of this invention have the further advantage of stabilizing oil and water emulsions and providing a good skinfeel.

Accordingly, a first element of compositions according to the present invention is that of a taurate copolymer. A particularly preferred copolymer is one wherein the taurate repeating monomer unit is acryloyl dimethyl taurate (in either free acid or salt form). Monomers forming the copolymer with taurate may include: styrene, acrylic acid, methacrylic acid, vinyl chloride, vinyl acetate, vinyl pyrrolidone, isoprene, vinyl alcohol, vinyl methylether, chloro-styrene, dialkylamino-styrene, maleic acid, acrylamide, methacrylamide and mixtures thereof. Where the term "acid" appears, the term means not only the free acid but also $C_1$–$C_{30}$ alkyl esters, anhydrides and salts thereof. Preferably but not exclusively the salts may be ammonium, alkanolammonium, alkali metal and alkaline earth metal salts. Most preferred are the ammonium and alkanolammonium salts.

Most preferred as the copolymer is Acryloyl Dimethyltaurate/Vinyl Pyrrolidone Copolymer, which is the INCI nomenclature, for a material supplied by Clariant Corporation under the trademark Aristoflex® AVC, having the following general formula:

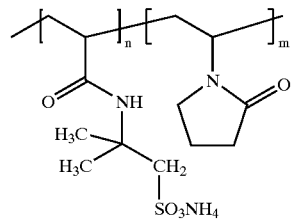

wherein n and m are integers which may independently vary from 1 to 10,000.

Average molecular weight of copolymers according to the invention may range from about 1,000 to about 3,000,000, preferably from about 3,000 to about 100,000, optimally from about 10,000 to about 80,000.

Amounts of the taurate copolymer may range from about 0.001 to about 10%, preferably from about 0.01 to about 8%, more preferably from about 0.1 to about 5%, optimally from about 0.2 to about 1% by weight of the composition.

A second element of the compositions according to the present invention is an alpha- or beta-hydroxycarboxylic acid or salt thereof. The former may be a $C_1$–$C_{25}$ alpha-hydroxycarboxylic acid of formula I

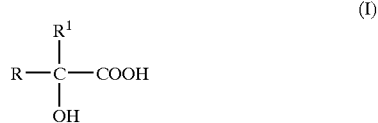

wherein R and $R^1$ are H, F, Cl, Br, alkyl, aralkyl or aryl groups being saturated or unsaturated, isomeric or nonisomeric, straight or branched chain, or in cyclic form having 5 or 6 ring members, and in addition, R and $R^1$ may carry OH, CHO, COOH and alkoxy groups having 1 to 9 carbon atoms, the α-hydroxyacid existing as a free acid or lactone form, or in salt form with an organic amine base or an inorganic alkali, and as stereoisomers, and D, L, and DL forms when R and $R^1$ are not identical.

Illustrative of this group of materials are 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxyhexanoic acid; 2-hydroxyheptanoic acid; 2-hydroxyoctanoic acid; 2-hydroxynonanoic acid; 2-hydroxydecanoic acid; 2-hydroxyundecanoic acid; 2-hydroxydodecanoic acid (α-hydroxylauric acid); 2-hydroxytetradecanoic acid (α-hydroxymyristic acid); 2-hydroxyhexadecanoic acid (α-hydroxypalmitic acid); 2-hydroxyoctadecanoic acid (α-hydroxystearic acid); 2-hydroxyeicosanoic acid (α-hydroxyarachidonic acid); 2-phenyl 2-hydroxyethanoic acid (mandelic acid); 2,2-diphenyl 2-hydroxyethanoic acid (benzilic acid); 3-phenyl 2-hydroxypropanoic acid (phenyllactic acid ); 2-phenyl 2-methyl 2-hydroxyethanoic acid (atrolactic acid); 2-(4'-hydroxyphenyl) 2-hydroxyethanoic acid; 2-( 4'-chlorophenyl 2-hydroxyethanoic acid; 2-(3'-hydroxy-4'-methoxyphenyl) 2-hydroxyethanoic acid; 2-(4'-hydroxy-3'-methoxyphenyl) 2-hydroxyethanoic acid; 3-( 2-hydroxyphenyl) 2-hydroxypropanoic acid; 3-(4'-hydroxyphenyl) 2-hydroxypropanoic acid; and 2-(3',4'-dihydroxyphenyl) 2-hydroxyethanoic acid.

Most preferred of this group of materials are glycolic acid, lactic acid, and 2-hydroxyoctanoic acids. The salts may be selected from alkalimetal, ammonium and $C_1$–$C_{20}$ alkyl or alkanolammonium counterions.

Advantageously, the hydroxycarboxylic acid will be fully neutralized as the potassium, sodium, ammonium or alkanolammonium salt. At least about 1%, preferably at least about 10% and optimally at least about 20% will be present as the salt form. Also effective are mixtures of acid and salt forms ranging in molar ratio from 1000:1 to 1:1000, preferably from 100:1 to 1:100, more preferably from 50:1 to 1:1, optimally from 20:1 to 2:1.

The beta-hydroxycarboxylic acids are best illustrated by salicylic acid and its derivatives. Levels of the hydroxycarboxylic acids may range from about 0.01 to about 20%, preferably from about 0.2 to about 10%, optimally from about 1 to about 5% by weight.

Compositions of the present invention may either be aqueous or anhydrous. Preferably the compositions are aqueous, especially water and oil emulsions of the W/O or O/W variety. Water when present will be in amounts which may range from about 5 to about 90%, preferably from about 35 to about 70%, optimally between about 40 and 60% by weight.

The pH of compositions of this invention is less than 7. Advantageously, pH may range from about 1 to about 6, preferably from about 2 to about 5, optimally from 2.5 to 3.8.

Emollient materials in the form of mineral oils, silicone oils and synthetic esters may be incorporated into compositions of the present invention. Amounts of the emollients may range anywhere from about 0.1 to about 30%, preferably between about 0.5 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C.

Among suitable ester emollients are:
(1) Alkenyl or alkyl esters of fatty acids having 10 to 20 carbon atoms. Examples thereof include isopropyl palmitate, isopropyl isostearate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate.
(5) Sterols esters, of which soya sterol and cholesterol fatty acid esters are examples thereof.

The most preferred esters are dicaprylyl ether and isopropyl isostearate.

Fatty acids having from 10 to 30 carbon atoms may also be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerin. The amount of humectant may range anywhere from 0.5 to 30%, preferably between 1 and 15% by weight of the composition.

Collectively the water, solvents, silicones, esters, fatty acids and/or humectants are viewed as cosmetically acceptable carriers for the compositions of the invention. Total amount of carrier will range from about 1 to 99.9%, preferably from about 80 to 99% by weight.

Cosmetic compositions of the present invention may be in any form. These forms may include lotions, creams, roll-on formulations, mousses, aerosol sprays and cloth- or pad-applied formulations.

Emulsifiers may also be present in cosmetic compositions of the present invention. Total concentration of the emulsifier will range from about 0.1 to about 40%, preferably from about 1 to about 20%, optimally from about 1 to about 5% by weight of the total composition. The emulsifier may be selected from the group consisting of anionic, nonionic, cationic and amphoteric actives. Particularly preferred non-ionic surfactants are those with a $C_{10}$–$C_{20}$ fatty alcohol or acid hydrophobe condensed with from about 2 to about 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, $C_8$–$C_{20}$ alkyl ether phosphates, alkylethercarboxylates and combinations thereof.

Sunscreen actives may also be included in compositions of the present invention. Particularly preferred are such materials as Avobenzene, available as Parsol® 1789, ethylhexyl p-methoxycinnamate, available as Parsol® MCX, and benzophenone-3, also known as Oxybenzone. Inorganic sunscreen actives may be employed such as microfine titanium dioxide, polyethylene and various other polymers. Amounts of the sunscreen agents will generally range from about 0.1 to about 30%, preferably from about 2 to about 20%, optimally from about 4 to about 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Co-thickening agents may be included in compositions of the present invention. Particularly useful are the polysaccharides. Examples include starches, natural/synthetic gums and cellulosics. Representative of the starches are chemically modified starches such as aluminum starch octenylsuccinate. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose.

Amounts of the co-thickener may range from about 0.001 to about 5%, preferably from about 0.1 to about 2%, optimally from about 0.2 to about 0.5% by weight.

For additional thickening, it is preferred to have magnesium aluminum silicate, commercially available as Veegum®, sold by the R.T. Vanderbilt Company. Amounts of this inorganic thickening agent may range from about 0.01 to about 10%, preferably from about 0.5 to about 1.2% by weight.

Minor adjunct ingredients may also be present in the cosmetic compositions. Among them may be the water-insoluble vitamins such as Vitamin A Palmitate, Vitamin E Acetate and DL-panthenol. Also useful are: retinol, ceramides and herbal extracts including green tea and chamomile.

Colorants, fragrances and abrasives may also be included in compositions of the present invention. Each of these substances may range from about 0.05 to about 5%, preferably between 0.1 and 3% by weight.

Compositions of the present invention advantageously will have viscosities ranging from about 500 to about 100,000, preferably from about 1,000 to about 60,000, optimally from about 1,500 to about 30,000 cps. These viscosities are measured on a Brookfield RVT Viscometer, Spindle 4, at 20 rpm and 23° C.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The following Examples will more fully illustrate the embodiments of this invention. All parts, percentages and proportions referred to herein and in the appended claims are by weight unless otherwise indicated.

EXAMPLES 1–8

Typical formulations according to the present invention are described below.

| Ingredients | Example (Weight %) | | | | | | | |
| --- | --- | --- | --- | --- | --- | --- | --- | --- |
| | 1 | 2 | 3 | 4 | 5 | 6 | 7 | 8 |
| Disodium EDTA | 0.05 | 0.05 | 0.05 | 0.05 | 0.05 | 0.05 | 0.05 | 0.05 |
| Methyl Paraben | 0.15 | 0.15 | 0.15 | 0.15 | 0.15 | 0.15 | 0.15 | 0.15 |
| Aloe Vera | 0.10 | 0.10 | 0.10 | 0.10 | 0.10 | 0.10 | 0.10 | 0.10 |
| Magnesium Aluminum Silicate | 0.60 | 0.60 | 0.60 | 0.60 | 0.60 | 0.60 | 0.60 | 0.60 |

-continued

| Ingredients | Example (Weight %) | | | | | | | |
|---|---|---|---|---|---|---|---|---|
| | 1 | 2 | 3 | 4 | 5 | 6 | 7 | 8 |
| Glycerin | 5.00 | 5.00 | 5.00 | 5.00 | 5.00 | 5.00 | 5.00 | 5.00 |
| Butylene Glycol | 2.00 | 2.00 | 2.00 | 2.00 | 2.00 | 2.00 | 2.00 | 2.00 |
| Xanthan Gum | 0.20 | 0.20 | 0.20 | 0.20 | 0.20 | 0.20 | 0.20 | 0.20 |
| Cetearyl Alcohol | 1.50 | 1.50 | 1.50 | 1.50 | 1.50 | 1.50 | 1.50 | 1.50 |
| Sorbitan Stearate | 1.10 | 1.10 | 1.10 | 1.10 | 1.10 | 1.10 | 1.10 | 1.10 |
| PEG-100 Stearate | 0.50 | 0.50 | 0.50 | 0.50 | 0.50 | 0.50 | 0.50 | 0.50 |
| Glyceryl Dilaurate | 0.50 | 0.50 | 0.50 | 0.50 | 0.50 | 0.50 | 0.50 | 0.50 |
| Stearic Acid | 3.00 | 3.00 | 3.00 | 3.00 | 3.00 | 3.00 | 3.00 | 3.00 |
| Sucrose Polystearate | 0.25 | 0.25 | 0.25 | 0.25 | 0.25 | 0.25 | 0.25 | 0.25 |
| Propylparaben | 0.10 | 0.10 | 0.10 | 0.10 | 0.10 | 0.10 | 0.10 | 0.10 |
| Tocopheryl Acetate | 0.10 | 0.10 | 0.10 | 0.10 | 0.10 | 0.10 | 0.10 | 0.10 |
| Ascorbyl Palmitate | 0.01 | 0.01 | 0.01 | 0.01 | 0.01 | 0.01 | 0.01 | 0.01 |
| Octyl Methoxycinnamate | 1.00 | 1.00 | 1.00 | 1.00 | 1.00 | 1.00 | 1.00 | 1.00 |
| Dimethicone | 1.00 | 2.00 | 1.00 | 0.50 | 3.00 | 1.00 | 5.00 | 1.00 |
| Dicaprylyl Ether | 4.00 | 3.00 | 6.00 | 6.00 | 2.00 | 3.00 | 0.50 | 0.50 |
| Isopropyl Isostearate | 1.50 | 1.50 | 1.50 | 1.50 | 1.50 | 1.50 | 1.50 | 1.50 |
| Glycolic Acid (80% Active) | 8.00 | 11.40 | 8.40 | 4.60 | 10.60 | 12.40 | 10.80 | 8.80 |
| Ammonium Hydroxide | 1.80 | 2.80 | 1.80 | 0.50 | 2.40 | 3.00 | 2.50 | 1.80 |
| Polymethyl Methacrylate | 0.50 | 0.50 | 0.50 | 0.50 | 0.50 | 0.50 | 0.50 | 0.50 |
| Aluminum Starch Octenylsuccinate | 2.00 | 2.00 | 3.00 | 1.50 | 0.50 | 3.00 | 2.50 | 2.00 |
| Acryloyl Dimethyltaurate Copolymer (7% Active) | 1.00 | 1.30 | 1.50 | 2.00 | 4.00 | 0.50 | 0.50 | 1.00 |
| Bisabolol | 0.10 | 0.10 | 0.10 | 0.10 | 0.10 | 0.10 | 0.10 | 0.10 |
| Retinol | 0.02 | 0.02 | 0.02 | 0.02 | 0.02 | 0.02 | 0.02 | 0.02 |
| Fragrance | 0.03 | 0.03 | 0.03 | 0.03 | 0.03 | 0.03 | 0.03 | 0.03 |
| Water | Balance | Balance | Balance | Balance | Balance | Balance | Balance | Balance |

EXAMPLE 9

A series of comparative experiments were conducted to measure the relative thickening effectiveness of various polymers in low pH systems containing hydroxycarboxylic acid. Table 1 reports a series of viscosity measurements on a gel solution consisting of 98% water and 2% thickener. Measurements were conducted using a Brookfield RVT instrument, Spindle No. 4 at 20 rpm and 23° C. The most efficient thickener was Aristoflex® AVC (Sample 1G).

TABLE 1*

| Sample | Thickener | Viscosity (cps) | pH |
|---|---|---|---|
| 1A | Sepigel ® 305 | 19,995 | 6.0 |
| 1B | Simulgel ® EG | 23,900 | 6.8 |
| 1C | Simulgel ® NS | 16,600 | 5.5 |
| 1D | Stabylen ® 30 | 15,850 | 2.9 |
| 1E | Synthalen ® CR | 27,750 | 4.0 |
| 1F | Carbopol ® 934 | 1,735 | 2.8 |
| 1G | Aristoflex ® AVC | 40,000 | 4.8 |

*2% Gel

The identities of the polymers in Table 1 are as follows:

| Thickener | INCI Name |
|---|---|
| Sepigel ® 305 | Polyacrylamide/C13–14 Isoparaffin/Laureth-7 |
| Simulgel ® EG | Sodium Acrylate/Sodium Acryloyldimethyl Taurate Copolymer/Isohexadecane/Polysorbate 80 |
| Simulgel ® NS | Hydroxyethyl Acrylate/Sodium Acryloyldimethyl Taurate Copolymer/Squalane/Polysorbate 60 |
| Stabylen ® 30 | Acrylates/Vinyl Isodecanoate Crosspolymer |
| Synthalen ® CR | Polyquaternium-37 (Quaternary Acrylic Polymer) |
| Carbopol ® 934 | Crosslinked Polyacrylate |
| Aristoflex ® AVC | Acryloyl Taurate/Vinyl Pyrrolidone Copolymer |

Table 2 reports the effect of adding glycolic acid (an alpha-hydroxycarboxylic acid) to each of the gel solutions. All of the thickened samples decreased in viscosity. However, the Synthalen® CR and Aristoflex® AVC samples still maintained a reasonable level of thickness.

TABLE 2*

| Sample | Thickener | Viscosity (cps) | pH |
|---|---|---|---|
| 1A | Sepigel ® 305 | <1,000 | 2.0 |
| 1B | Simulgel ® EG | <100 | 2.1 |
| 1C | Simulgel ® NS | <100 | 2.0 |
| 1D | Stabylen ® 30 | <100 | 1.9 |
| 1E | Synthalen ® CR | 17,450 | 1.7 |
| 1F | Carbopol ® 934 | <100 | 1.9 |
| 1G | Aristoflex ® AVC | 20,500 | 2.0 |

*2% Gel + 8% Glycolic Acid

Tables 3 and 4 illustrates the effect of partially neutralizing the glycolic acid with ammonium hydroxide to result in a partially neutralized acid solution of glycolic acid/ammonium glycolate. In these highly stressed, low pH systems, only the Aristoflex® AVC provided even a modest measure of thickening to the hydroxycarboxylic acid systems.

TABLE 3*

| Sample | Thickener | Viscosity (cps) | PH |
|---|---|---|---|
| 1A | Sepigel ® 305 | <1,00 | 3.0 |
| 1B | Simulgel ® EG | <100 | 3.0 |
| 1C | Simulgel ® NS | <100 | 3.0 |
| 1D | Stabylen ® 30 | <100 | 3.0 |
| 1E | Synthalen ® CR | 3,650 | 2.9 |
| 1F | Carbopol ® 934 | <100 | 3.0 |
| 1G | Aristoflex ® AVC | 9,060 | 3.0 |

*2% Gel + 8% Glycolic Acid/Ammonium Glycolate (acid to salt molar ratio of 10:1)

TABLE 4*

| Sample | Thickener | Viscosity (cps) | PH |
|---|---|---|---|
| 1A | Sepigel ® 305 | <100 | 3.6 |
| 1B | Simulgel ® EG | <100 | 3.6 |
| 1C | Simulgel ® NS | <100 | 3.5 |
| 1D | Stabylen ® 30 | 1,445 | 3.5 |
| 1E | Synthalen ® CR | <100 | 3.5 |
| 1F | Carbopol ® 934 | <100 | 3.5 |
| 1G | Aristoflex ® AVC | 2,555 | 3.6 |

*2% Gel + 8% Glycolic Acid/Ammonium Glycolate (acid to salt molar ratio of 3.4:1)

The foregoing description and examples illustrate selected embodiments of the present invention. In light thereof variations and modifications will be suggested to one skilled in the art, all of which are within the spirit and purview of this invention.

What is claimed is:

1. A cosmetic composition comprising:
    (i) from about 0.01 to 20% of a $C_1$–$C_{25}$ alpha- or beta-hydroxy carboxylic acid at least partially present as a salt thereof and wherein the carboxylic acid and salt thereof are present in a respective molar ratio of 20:1 to 2:1;
    (ii) from about 0.01 to about 10% of a taurate copolymer which is acryloyl dimethyl taurate/vinylpyrrolidone copolymer; and
    (iii) a cosmetically acceptable carrier, wherein the composition has a pH of less than 7.

2. A composition according to claim 1 wherein the $C_2$–$C_{25}$ alpha-hydroxy carboxylic acid is selected from the group consisting of glycolic acid, lactic acid, 2-hydroxyoctanoic acid and combinations thereof.

* * * * *